United States Patent [19]

Robinson et al.

[11] 4,102,667

[45] Jul. 25, 1978

[54] ADDITIVE AND METHOD FOR REDUCING THE DRIFT OF AQUEOUS SPRAY COMPOSITIONS

[75] Inventors: Robert Earl Robinson, Columbia; John Alan Ernst, Lexington, both of S.C.

[73] Assignee: Lindau Chemicals, Inc., Columbia, S.C.

[21] Appl. No.: 706,043

[22] Filed: Jul. 16, 1976

[51] Int. Cl.$^2$ ............................................. C08L 9/00
[52] U.S. Cl. ................................... 71/3; 71/64 C; 71/64 G; 71/DIG. 1; 260/29.7 H; 260/29.7 EM; 526/271; 526/338
[58] Field of Search .............. 260/29.7 H, 29.7 EM; 526/271, 338; 71/64 G, 64 C, DIG. 1, 3

[56] References Cited

U.S. PATENT DOCUMENTS

| | | | |
|---|---|---|---|
| 3,002,940 | 10/1961 | Holloway | 526/271 |
| 3,445,065 | 5/1969 | Waldrum | 239/171 |
| 3,491,068 | 1/1970 | Gaylord | 526/218 |
| 3,523,646 | 8/1970 | Waldrum | 239/171 |
| 3,624,019 | 11/1971 | Anderson et al. | 260/29.6 B |
| 3,692,512 | 9/1972 | Sachnik | 71/27 |
| 3,812,619 | 5/1974 | Wood et al. | 71/64 G |

*Primary Examiner*—M. J. Welsh
*Attorney, Agent, or Firm*—Lawrence Rosen; E. Janet Berry

[57] ABSTRACT

An additive composition containing a substantially water-soluble, alternating copolymer of maleic acid and a conjugated diene such as butadiene for reducing the drift of aqueous spray compositions. Certain salts of the copolymer may also be employed and the aqueous spray compositions may either be water or water-containing compositions containing herbicides, plant growth regulators, fungicides, insecticides, bactericides, fertilizers, defoliants, seeds, and the like as well as mixtures thereof. The drift-inhibiting additive compositions of this invention may also be used in conjunction with water-based paints. A method of dispensing aqueous compositions on the ground utilizing the drift-inhibiting additive compositions is also encompassed by the invention.

13 Claims, No Drawings

ADDITIVE AND METHOD FOR REDUCING THE DRIFT OF AQUEOUS SPRAY COMPOSITIONS

The present invention pertains to an additive composition for aqueous spray compositions which will reduce the tendency of the sprayed aqueous droplets to drift and which will avoid clogging the spray nozzles. More particularly, the invention relates to the use of substantially water-soluble, alternating copolymers of maleic acid and a conjugated diene for controlling the size of aqueous droplets discharged from various spraying devices including those adapted for aerial and land spraying operations.

BACKGROUND OF THE INVENTION

Several problems have been encountered in spraying aqueous compositions. The problem of "drift" is well known in connection with the aerial spraying of water during fire fighting operations and the spraying of aqueous solutions of agrochemicals such as systemic herbicides, plant growth regulators, pesticides, insecticides, and the like. Another problem is the clogging of the spray nozzles after the spraying operations have commenced which may result from the presence of certain commercially available polymeric concentrates which have been added to the aqueous spray composition to minimize the drift problem. Although the problems of drift and clogging of spray nozzles are especially troublesome in aerial spraying for obvious reasons, both problems are also troublesome with hand-held or land operated equipment.

As set forth in U.S. Pat. Nos. 3,445,065 and 3,523,646, it is well recognized that the problem of drift is particularly acute when many fine droplets are produced in a spraying operation, since the fine droplets are more easily carried away and are dispersed over a greater area by winds, drafts, etc. than the larger droplets. Reference is made to the "Handbook on Aerial Application in Agriculture" published by the A & M College of Texas, College Station, Tex. in December, 1956. This handbook further discusses the desirability of shortening the time in which the droplets are in the air in order to decrease drift. In addition to increasing droplet size to overcome the drift problem, other suggestions include the use of special spray devices including those which will produce uniform droplet size. It has also been recognized that a mere increase in droplet size will not always prove effective, since as the droplet size is increased there is often a concomitant tendency for droplet dissociation to occur with undesirable formation of small droplets which will drift with winds, drafts, etc. In aerial spraying of systemic herbicides there has been a proposal to use a very heavy invert herbicide emulsion with the expectation that only large heavy droplets would be formed during spraying. As will be appreciated, the preparation and spraying of invert emulsions involves additional time and increases the cost of the spraying operations. The viscous carrier fluids for such systems are invert emulsion liquid polyacrylic terpolymer concentrates as disclosed in U.S. Pat. No. 3,624,019. These polymeric concentrates are sold under the trademarks "LoDrift" by Amchem Products, Inc. and "EnDrift" by Nalco Chemical Company.

In a recent proposal for cutting down drift it has been suggested to add to the aqueous spray composition a drift reduction agent sold under the trademark "Target" by Loveland Industries, Inc., the principal functioning agent being identified as a polyethylene polymer. It has been found however that the use of such a drift reduction agent or hydrocarbon polymer emulsions tends to cause clogging of the spray nozzles and also requires frequent agitation of the additive-containing, aqueous spray composition, particularly when there is a significant time lapse between formulation and actual spraying or when the spraying is carried out for a long period of time.

One object of the present invention is to provide an additive for aqueous spray compositions which will reduce the drift of the spray without encountering the problems associated with the previous proposals.

Another object of the invention is to provide an additive for aqueous spray compositions which will enhance the formation of large, stable droplets.

A further object of the invention is to provide a drift reducing additive for use in conjunction with aqueous spray compositions which neither requires special spraying devices nor causes clogging of the spray nozzles.

A still further object of the invention is to provide a method for aerial spraying utilizing an aqueous spray composition, which may or may not contain water-soluble or water-suspended agrochemicals, containing a drift reduction additive.

An additional object of the invention is to provide a method for aerial sowing of seeds utilizing an aqueous spray composition containing a drift reduction additive.

These and other objects of the present invention are achieved by providing a drift reducing additive for aqueous spray compositions, said additive being a substantially water-soluble, predominantly cis-1,4 alternating copolymer of maleic acid and a conjugated diene prepared by hydrolyzing the corresponding predominantly cis-1,4 alternating copolymer of maleic anhydride and a conjugated diene. Both of these copolymeric materials as well as the hydrolysis procedure for converting the maleic anhydride-conjugated diene copolymer to the maleic acid-conjgated diene copolymer or salt thereof are disclosed in U.S. Pat. No. 3,491,068, all of the disclosure of this patent being incorporated herein by reference. Examples I through XI of U.S. Pat. No. 3,491,068 show the /preparation of these particular maleic anhydride copolymers with various conjugated dienes, Example XVI illustrates the hydrolysis of the maleic anhydride-conjugated diene copolymers to form the maleic acid-diene copolymers, and Example XVII illustrates the conversion of the maleic anhydride copolymers to various maleic acid-diene copolymer salts. It will be understood however that neither the preparation of the copolymers nor their conversion to the acid or to the salt forms constitute essential features of the present invention.

The conjugated dienes which are useful for preparing the copolymers comprise compounds having the following structural formula:

$$RCH{=}\overset{R_1}{\overset{|}{C}}{-}\overset{R_2}{\overset{|}{C}}{=}CHR_3$$

where R, $R_1$, $R_2$, and $R_3$, which may be the same or different, represent a member of the group consisting of hydrogen, halogen, alkoxyl, aryl, cycloalkyl or alkyl radicals having from 1 to 40 carbon atoms, and preferably from about 1 to 8 carbon atoms. Illustrative conjugated dienes include butadiene, isoprene, 2-chloro-1,3- butadiene, 2,3-dichlorobutadiene, 2,3-dimethylbutadiene, piperylene, 2,4-hexadiene, 2-methyl-1,3-pentadiene, 2-ethyl-1,3-butadiene, 2-propyl-1,3-butadiene, 2-phenyl-1,3-butadiene, 3-methyl-1,3-pentadiene, 2-ethyl-1,3-pentadiene, 2-methyl-1, 3-hexadiene, 1-methoxy-1,3-butadiene, etc. The use of butadiene, isoprene, 2-chloro-1, 3-butadiene, and piperylene is especially preferred, since the resulting maleic anhydride copolymers are inexpensive, easily prepared and readily converted to derivatives. In general, the molar ratio of conjugated diene to the maleic anhydride will range from about 5:1 to 1:5, and preferably about 1:1 since it was determined that the copolymers contain maleic anhydride and the conjugated diene in a 1:1 molar ratio, regardless of the starting ratio. For some purposes, however, it may be desirable to employ an excess of either of these reactants. The preferred conjugated diene is butadiene.

The reaction between the maleic anhydride and the conjugated diene to produce the alternating, predominantly cis-1,4 copolymer is carried out in accordance with the methods described in columns 3, 4, and 5 of U.S. Pat. No. 3,491,068. The resulting alternating copolymers of the conjugated diene and the maleic anhydride have a structure containing as the predominant recurring unit:

$$\begin{array}{c} R_1\ R_2 \\ R\ \ \ C{=}C\ \ \ R_3\ \ \ H\ \ \ H \\ \diagdown\!\diagup\ \ \ \diagdown\!\diagup \\ -C\ \ \ \ \ \ \ \ \ \ \ \ C-C-C- \\ |\ \ \ \ \ \ \ \ \ \ \ \ \ |\ \ \ |\ \ \ | \\ H\ \ \ \ \ \ \ \ \ \ \ H\ \ \ C\ \ \ \ C \\ \diagup\diagdown\diagup\diagdown \\ O\ \ \ \ O\ \ \ \ O \end{array}$$

where R, $R_1$, $R_2$, and $R_3$ are as previously defined. The unsaturation in the copolymer has at least 75% and generally about 85–95% of the cis-1,4 structure.

Conventional hydrolysis processes may be utilized to convert the maleic anhydride-conjugated diene copolymer to the maleic acid acid-conjugated diene copolymer. One such method comprises adding the maleic anhydride-conjugated diene to an excess of distilled water followed by heating to a temperature of at least 70° C., preferably about 95° to 100° C., for about 1 to 10 hours. The resulting maleic acid-conjugated diene may be utilized in solution as formed.

The conversion of the maleic anhydride-conjugated diene copolymer to the maleic acid salt derivatives is accomplished by treating the aqueous solution of the polymeric acid with alkali metal or alkaline earth metal hydroxides or carbonates, the metals being selected, for example, from the group consisting of sodium, potassium, lithium, calcium, barium, strontium, and magnesium. When ammonium derivatives are desired aqueous solutions of ammonia may be utilized. Solutions of the resulting salts may be used directly in the practice of the present invention.

The maleic acid-conjugate diene copolymers or their derivatives which will function as the drift reducing additives of this invention have the following structural formula:

$$\begin{array}{c} R_1\ R_2 \\ R\ \ \ C{=}C\ \ \ R_3\ \ \ H\ \ \ H \\ \diagdown\!\diagup\ \ \ \diagdown\!\diagup \\ -C\ \ \ \ \ \ \ \ \ \ \ \ C-C-C- \\ |\ \ \ \ \ \ \ \ \ \ \ \ \ |\ \ \ |\ \ \ | \\ H\ \ \ \ \ \ \ \ \ \ \ H\ \ \ O{=}C\ \ \ C{=}O \\ \ \ \ \ \ \ \ \ \ \ \ \ \ \ \ \ \ \ \ \ \ |\ \ \ \ \ \ \ | \\ \ \ \ \ \ \ \ \ \ \ \ \ \ \ \ \ \ \ \ \ \ X\ \ \ \ \ Y \end{array}$$

wherein R, $R_1$, $R_2$, and $R_3$ are as defined above or preferably are members selected from the group consisting of hydrogen, halogen, aryl radicals and alkyl, cycloalkyl and alkoxyl radicals having from 1 to 8 carbon atoms and wherein R, $R_1$, $R_2$, and $R_3$ are the same or different and wherein at least 75% of the carbon-to-carbon double bond structure is cis-1,4; and wherein X and Y are OZ and wherein Z is hydrogen, an alkali or alkaline earth metal, or an ammonium radical, and wherein Z is the same or different.

In the preferred embodiment of the invention, an aqueous solution of the maleic acid-conjugated diene copolymer or its salt derivative is added directly to the aqueous spray composition. It is also possible to first isolate the acid or the salt by conventional chemical techniques, and to employ the isolated product in dry form as the desired additive.

Regardless of the manner in which the maleic acid copolymer or its salt is added to the aqueous spray composition, the amount of additive generally employed will range from about 0.01 to 0.10% by volume based on the total volume of the aqueous spray composition. Preferred amounts will range from about 0.03 to 0.06% by volume. When an aqueous additive composition is preformed, the amount of additive or functioning agent in this solution will range from about 10 to 50% by volume, preferably from about 20 to 30% by volume. The aqueous additive composition is then added to the aqueous spray composition in amounts of from about 0.3 to 6 parts, preferably from about 1.25 to 2.5 parts by volume per 1000 parts by volume of the aqueous spray composition.

For most purposes it is preferred to use the free acid maleic acid-conjugated diene copolymers, but in some instances when corrosion may occur the alkali metal, alkaline earth metal or ammonium salt derivatives can be utilized.

The use of these maleic acid-conjugated diene copolymers or salts thereof to attain increased spray droplet size is unexpected and surprising since organic polymers with chains containing polar groups such as carboxyl groups or salts thereof generally display detergent characteristics. The effect of detergents on aqueous spray compositions is usually expected to reduce the size of the droplets which is exactly the opposite effect attained by using the above described alternating copolymers and their salts.

The drift reduction agent of this invention may be employed with a variety of aqueous spray compositions. Thus, for example, the aqueous spray composition may comprise essentially a water spray useful for fire fighting purposes. Such water compositions may of course contain any of the usual additives that are employed in aqueous, fire fighting spray compositions. As previously mentioned, the aqueous spray compositions may contain various agrochemicals or mixtures thereof. Typical agrochemicals include water-soluble herbicides, plant growth regulators, fungicides, insecticides, bactericides, fertilizers, defoliants, etc. as well as mixtures thereof. These agrochemicals will be present in the aqueous spray compositions in conventional amounts such as 1 to 20% by volume based on the total volume of the aqueous spray composition. Illustrative herbicides include 2,4-dichlorophenoxyacetic acid and its salts or esters; ammonium sulfamate; 2,4,5-trichlorophenoxypropionic acid, its salts and esters; and 2,4-bis (isopropylamino)-6-methoxy-s-triazine. An illusrtrative plant growth regulator is sodium ferric diethylenetriamine pentacetate. Illustrative fungicides include N-[(trichloromethyl)thio]-4-cyclohexene-1,2-dicarboximide, zinc or manganese ethylene bisdithiocarbamate, and copper sulfate. Illustrative insecticides include O,O-dimethyldithiophosphate of diethyl mercaptosuccinate, and octachloro-4,7-methanotetrahydroindane. An illustrative bactericide is N-alkyl dimethylbenzylammonium chloride. Illustrative fertilizers include ammonium nitrate and ammoniated phosphate. Defoliants such as tributyl phosphorotrithioate and tributyl phosphorotrithioite may also be employed. Wheat and soybean seeds suspended in water may, for example, be employed in aerial seeding in accordance with the practice of this invention.

Neither the choice of a particular agrochemical nor the amount of agrochemical employed is a critical feature of the present invention.

In accordance with another feature of the present invention it has been found advantageous to employ the maleic acid-conjugated diene copolymers or salts thereof as drift reduction agents for water-based paints to minimize waste and to avoid needless contamination of adjacent areas with paint particles. For such purposes the amount of the maleic acidconjugated diene copolymer or salt thereof employed will generally be within the ranges set forth above. Typical water-based paints are the polyester-based and acrylic-based latex paints.

The invention will be more fully understood by reference to the following illustrative examples:

EXAMPLE 1

A solution of copolymer of butadiene with maleic anhydride made by the process of Example VIII of U.S. Pat. No. 3,491,068 is hydrolyzed to the free acid with boiling water in about one hour, and dissolved in three times its weight of water. The resulting solution is added to water at a level of two parts by volume of additive solution per 1000 parts by volume of water. From a hand-held spray gun, the resulting spray travels significantly faster and scatters less than does untreated water. The resulting solution when sprayed downward travels to the ground much more quickly than untreated water with considerably less evidence of a drift pattern. When sprayed from a helicopter onto a field at a height of 4 to 10 feet, in the presence of absence of the wind, there is substantially less tendency for the spray to drift than in the case of untreated spray. Similar results are noted in aerial spraying of systems containing common agricultural chemicals such as 2,4-dichlorophenoxyacetic acid and/or its salts or esters.

EXAMPLE 2

The copolymer of butadiene and maleic acid described in Example 1 is neutralized with concentrated ammonia and the resulting solution is adjusted to 25% concentration. Addition of 0.2% of this solution to water produces results in hand-held spraying experiments which are much superior to those attained with untreated water, as does spraying from a helicopter at 4 to 10 feet above the ground. More particularly, the horizontally sprayed material travels faster with less scattering than pure water. Spraying from a helicopter leads to more rapid dropping and a reduction in drifting, as compared to an untreated water.

EXAMPLE 3

The copolymer of butadiene and maleic acid described in Example 1 is neutralized with sodium hydroxide, and thereby converted to its sodium salt. This is adjusted to 25% concentration and added to water at a level of two parts by volume per 1000 parts by volume of water. When sprayed horizontally the material travels faster and scatters less than does pure water; and when directed toward the ground, such a spray drops more rapidly and demonstrates less tendency to drift than untreated water.

EXAMPLE 4

The 25% solution of copolymer of butadiene and maleic acid described in Example 1 is added at a level of 0.2% to an acrylic latex paint (Sears Colorhouse Latex Semi-Gloss Enamel). The resulting material displays a markedly reduced tendency to produce fine mist when sprayed horizontally or vertically, thereby being much more easily directed toward the area to be painted and reducing both paint consumption and the likelihood of breathing paint mist.

While particular embodiments of this invention are shown above, it will be understood that the invention is obviously subject to variations and modifications without departing from its broader aspects.

What is claimed is:

1. A method for depositing an aqueous composition in a well defined pattern in an area on the ground from above the ground comprising the steps of providing a mixture of said aqueous composition and a drift-inhibiting amount of a substantially water-soluble copolymer of maleic acid and a conjugated diene, said copolymer having the structural formula $$\begin{array}{c} R_1 \ R_2 \\ | \ \ | \\ R \ \ C=C \ \ R_3 \ \ H \ \ H \\ | \ / \ \ \ \ \ \ \ \ \backslash | \ \ | \ \ | \\ -C \ \ \ \ \ \ \ \ \ \ \ C\!-\!\!-\!\!C\!-\!\!C\!- \\ | \ \ \ \ \ \ \ \ \ \ \ \ \ \ \ | \ \ | \ \ | \\ H \ \ \ \ \ \ \ \ \ \ \ HO\!=\!C \ \ C\!=\!O \\ \ \ \ \ \ \ \ \ \ \ \ \ \ \ \ \ \ \ \ \ \ | \ \ | \\ \ \ \ \ \ \ \ \ \ \ \ \ \ \ \ \ \ \ \ \ \ X \ \ Y \end{array}$$

wherein R, $R_1$, $R_2$, and $R_3$ are members selected from the group consisting of hydrogen, halogen, aryl radicals and alkyl, cycloalkyl and alkoxy radicals having from 1 to 8 carbon atoms and wherein R, $R_1$, $R_2$, and $R_3$ are the same or different and wherein at least 75% of the carbon-to-carbon double bond structure is cis-1,4; and wherein X and Y are OZ and wherein Z is hydrogen, an alkali or alkaline earth metal, or an ammonium radical and wherein Z is the same or different; and dispensing the resulting admixture as aqueous droplets into the air above said area, said copolymer reducing drift of said aqueous droplets by increasing the droplet size.

2. The method of claim 1 wherein the amount of copolymer in the aqueous composition ranges from about 0.01 to 0.10% by volume.

3. The method of claim 1 wherein said conjugated diene is butadiene.

4. The method fo claim 1 wherein said aqueous composition comprises essentially water.

5. The method fo claim 1 wherein said aqueous composition also contains a water-soluble or water-suspended herbicide.

6. The method of claim 1 wherein said aqueous composition also contains a water-soluble or water-suspended plant growth regulator.

7. The method of claim 1 wherein said aqueous composition also contains a water-soluble or water-suspended fungicide.

8. The method of claim 1 wherein said aqueous composition also contains a water-soluble or water-suspended insecticide.

9. The method of claim 1 wherein said aqueous composiiton also contains a water-soluble or water-suspended bactericide.

10. The method of claim 1 wherein said aqueous composition also contains a water-soluble or water-suspended fertilizer.

11. The method of claim 1 wherein said aqueous composition also contains a water-soluble or water-suspended defoliant.

12. The method of claim 1 wherein said aqueous composition also contains water-suspended agricultural crop seeds.

13. A method for depositing an aqueous composition in a well defined pattern in an area on the ground from above the ground comprising the steps of providing a mixture of said aqueous composition and a drift-inhibiting amount of a substantially water-soluble, predominantly cis-1, 4 alternating copolymer of maleic acid and a conjugated diene having the formula:

$$RCH=\overset{R_1}{\underset{|}{C}}-\overset{R_1}{\underset{|}{C}}=CHR_3$$

wherein R, $R_1$, $R_2$, and $R_3$ are members selected from the group consisting of hydrogen, halogen, aryl radical and alkyl, cycloalkyl and alkoxyl radicals having from 1 to 8 carbon atoms, and wherein R, $R_1$, $R_2$, and $R_3$ are the same or different; and dispensing the resulting admixture as aqueous droplets into the air above said area, said copolymer reducing drift of said aqueous droplets by increasing the droplet size.

* * * * *